US009463104B2

(12) United States Patent
Siegel et al.

(10) Patent No.: US 9,463,104 B2
(45) Date of Patent: Oct. 11, 2016

(54) VASCULAR GRAFT DEVICE PLACEMENT METHODS

(71) Applicant: CEDARS-SINAI MEDICAL CENTER, Los Angeles, CA (US)

(72) Inventors: Robert James Siegel, Beverly Hills, CA (US); Jean Marzelle, Paris (FR)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 14/896,095

(22) PCT Filed: Jun. 6, 2014

(86) PCT No.: PCT/US2014/041366
§ 371 (c)(1),
(2) Date: Dec. 4, 2015

(87) PCT Pub. No.: WO2014/197839
PCT Pub. Date: Dec. 11, 2014

(65) Prior Publication Data
US 2016/0120673 A1    May 5, 2016

Related U.S. Application Data

(60) Provisional application No. 61/832,614, filed on Jun. 7, 2013, provisional application No. 61/874,921, filed on Sep. 6, 2013, provisional application No. 61/890,072, filed on Oct. 11, 2013.

(51) Int. Cl.
*A61F 2/06* (2013.01)
*A61F 2/95* (2013.01)
(Continued)

(52) U.S. Cl.
CPC ............ *A61F 2/95* (2013.01); *A61B 17/12109* (2013.01); *A61B 17/12118* (2013.01); *A61F 2/07* (2013.01); *A61F 2/958* (2013.01); *A61F 2/962* (2013.01); *A61B 2017/1205* (2013.01)

(58) Field of Classification Search
CPC .............. A61F 2/06; A61F 2/07; A61F 2/95; A61F 2/954; A61F 2/958; A61F 2/966; A61F 2002/072; A61F 2002/075; A61F 2002/077; A61F 2002/061; A61F 2002/9528; A61F 2002/9534; A61F 2002/9505; A61F 2002/9511; A61F 2002/9517; A61F 2002/9522; A61F 2002/9583; A61F 2002/9586; A61M 1/10; A61M 1/12; A61M 25/0194; A61M 2025/0197; A61B 17/121098; A61B 17/12113; A61B 17/12118; A61B 2017/1205

See application file for complete search history.

(56) References Cited

U.S. PATENT DOCUMENTS 6,325,819 B1    12/2001   Pavcnik et al.
6,464,665 B1 *  10/2002   Heuser ............... A61B 7/11
                                              604/101.01

(Continued)

FOREIGN PATENT DOCUMENTS

WO    WO 2012/061809    5/2012
WO    WO 2014/197839    12/2014

OTHER PUBLICATIONS

International Search Report and Written Opinion issued in PCT Application No. PCT/US2014/041366, dated Jan. 29, 2015, in 15 pages.

*Primary Examiner* — Jonathan Miles
*Assistant Examiner* — Kendra Obu
(74) *Attorney, Agent, or Firm* — Knobbe Martens Olson & Bear LLP

(57) ABSTRACT

In another embodiment, a method is provided for positioning a graft device in an ascending aorta of a patient. In the method, access is provided to a peripheral venous site. A first catheter is advanced through the peripheral venous site to a right atrium of the patient. Access is provided to the left atrium across an intra-atrial septum. The first catheter is advanced through to a left atrium of a patient. A second catheter is advanced from the first catheter through a left ventricle and the aorta to a peripheral arterial site. A graft device disposed on, over or within the second catheter is advanced from the peripheral venous site or the peripheral arterial site until the graft device reaches an ascending aorta of the patient. The graft device is positioned at a treatment site within the ascending aorta. The first and second catheters are removed from the patient.

23 Claims, 14 Drawing Sheets

(51) Int. Cl.
*A61B 17/12* (2006.01)
*A61F 2/07* (2013.01)
*A61F 2/958* (2013.01)
*A61F 2/962* (2013.01)

(56) References Cited

U.S. PATENT DOCUMENTS

| | | |
|---|---|---|
| 6,723,116 B2 | 4/2004 | Taheri |
| 6,746,464 B1 | 6/2004 | Makower |
| 7,488,344 B2 | 2/2009 | Hartley et al. |
| 8,267,986 B2 | 9/2012 | Berez et al. |
| 2005/0288765 A1 | 12/2005 | Taheri |
| 2006/0089704 A1 | 4/2006 | Douglas |
| 2006/0241748 A1 | 10/2006 | Lee et al. |
| 2009/0082609 A1 | 3/2009 | Condado |
| 2009/0177262 A1 | 7/2009 | Oberti et al. |
| 2010/0234932 A1 | 9/2010 | Arbefeuille et al. |
| 2010/0249918 A1 | 9/2010 | Zhang |
| 2011/0257731 A1 | 10/2011 | Hartley et al. |
| 2011/0270376 A1* | 11/2011 | Hartley .............. A61F 2/07 623/1.11 |
| 2012/0179097 A1 | 7/2012 | Cully et al. |
| 2012/0232585 A1 | 9/2012 | Roue et al. |
| 2013/0046371 A1* | 2/2013 | Greenberg .......... A61F 2/07 623/1.11 |

* cited by examiner

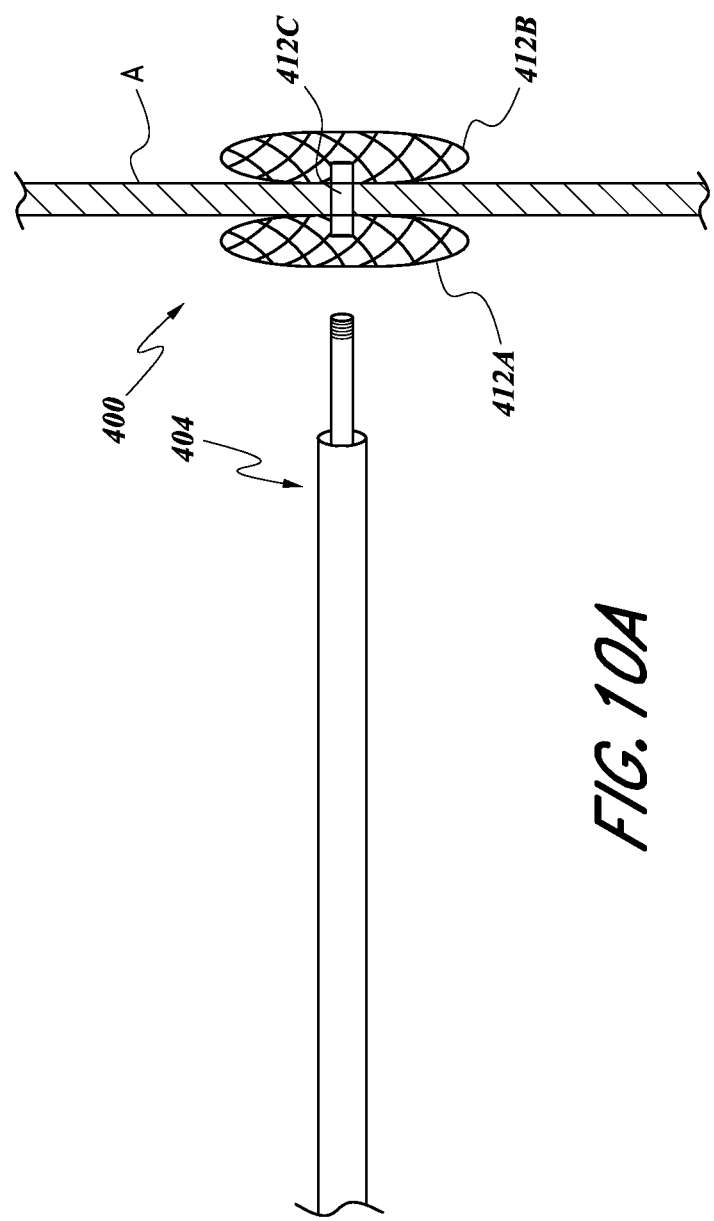

VASCULAR GRAFT DEVICE PLACEMENT METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

This application is directed to a system and method for placement of a medical device in blood vessels adjacent to the heart, for instance the ascending aorta.

2. Description of the Related Art

Aneurysm and dissection are potentially life threatening conditions in which a blood vessel becomes compromised. An aneurysm is an enlargement of the vessel, which can burst causing internal bleeding. Large arteries close to the heart may be at higher risk for aneurysm due to higher and more variable pressures. Large vessel aneurysms are particularly dangerous because internal bleeding can be massive and rapid. A dissection of a high volume blood vessel is potentially life threatening. A dissection can be described as a tear or breach in a vessel wall through which blood can flow into surrounding tissues.

While aneurysm and dissection can be treated with surgery, not all patients are good candidates for surgery. In fact, the International Registry of Acute Aortic Dissection reports that 28% of all patients are poor candidates for surgery. If given the choice, patients generally prefer to be treated with catheter procedures over surgery due to lower trauma and faster recovery. Catheter procedures can be faster than surgery as well. Shorter procedure and recovery times help produce outcomes that are less costly to the medical system overall, which is beneficial.

While catheter-based treatments of the descending aorta are known, these procedures are not well adapted for treating maladies of the ascending aorta, such as dissection and aneurysm.

SUMMARY OF THE INVENTION

In one embodiment, a system is provided for positioning a stent graft or other grafting device in an ascending aorta of a patient. The system has a first catheter, a second catheter, and a graft deployment zone. The first catheter has a length sufficient to extend from a peripheral venous site to a heart of the patient. The second catheter has a length sufficient to extend from the peripheral venous site, through the heart of the patient, to a peripheral arterial site. The graft deployment zone is disposed on at least one of the first and second catheter. For instance, the graft deployment zone can be disposed on the first catheter, the second catheter, or partly on first and partly on the second catheter. The deployment zone is adapted to be positioned in the aorta when the first and second catheters are extended through the vasculature of a patient. The deployment zone can be positioned in the ascending aorta, e.g., between the heart and the aortic arch. The system also can include a stent graft positioned in or on at least one of the first and second catheters.

In another embodiment, a system is provided for positioning a device in an ascending aorta of a patient. The system has a first elongate body, a second elongate body, and a device deployment platform. The first elongate body has a length sufficient to extend from a peripheral venous site to a heart of the patient. The second elongate body comprising a first zone configured to extend through the first elongate body from the peripheral venous site to the heart and a second zone configured to extend from at least a portion of the ascending aorta toward a peripheral arterial site, and optionally out of the body through the peripheral arterial site. The device deployment platform disposed on or in at least one of the first and the second elongate bodies, the deployment zone positioned between an aortic arch and the ascending aorta.

In another embodiment, a method is provided for positioning a graft device in an ascending aorta of a patient. In the method, access is provided to a peripheral venous site. A first catheter is advanced through the peripheral venous site to a right atrium of the patient. Access is provided to the left atrium across an intra-atrial septum. The first catheter is advanced through to a left atrium of a patient. A second catheter is advanced from the first catheter through a left ventricle and the aorta to a peripheral arterial site. A graft device disposed on, over or within the second catheter is advanced from the peripheral venous site or the peripheral arterial site until the graft device reaches an ascending aorta of the patient. The graft device is positioned at a treatment site within the ascending aorta. The first and second catheters are removed from the patient.

In another embodiment a method for positioning a device in a blood vessel of a patient adjacent to the heart is provided. A first catheter is advanced endoluminally to the heart. A second catheter is advanced from the first catheter through a valve in the heart to a blood vessel adjacent to the heart. A device is deployed from the second catheter within the blood vessel adjacent to the heart.

In another embodiment, a method is provided. In the method a device is positioned in a blood vessel of a patient adjacent to the heart. In the method a flow directed device is advanced into the cardiovascular system at an upstream location. The upstream location is located upstream of a treatment site adjacent to the aortic arch. A capture device is advanced into the cardiovascular system at a downstream location. The downstream location is downstream of the treatment site. The flow directed device is captured with the capture device. In one variation, the capturing provides a track from the upstream location to the downstream location. In another variation, the capturing facilitates replacing the flow directed device and capture device with a track from the upstream location to the downstream location. A treatment device is deployed at the treatment site from a delivery device advanced along the track.

BRIEF DESCRIPTION OF THE DRAWINGS

FIG. 10A illustrates a septum closure system and step in connection with certain embodiments;

More detailed descriptions of various embodiments of heart-adjacent device placement systems, components and methods useful to treat patients are set forth below.

DETAILED DESCRIPTION OF THE PREFERRED EMBODIMENT

Figure 1:
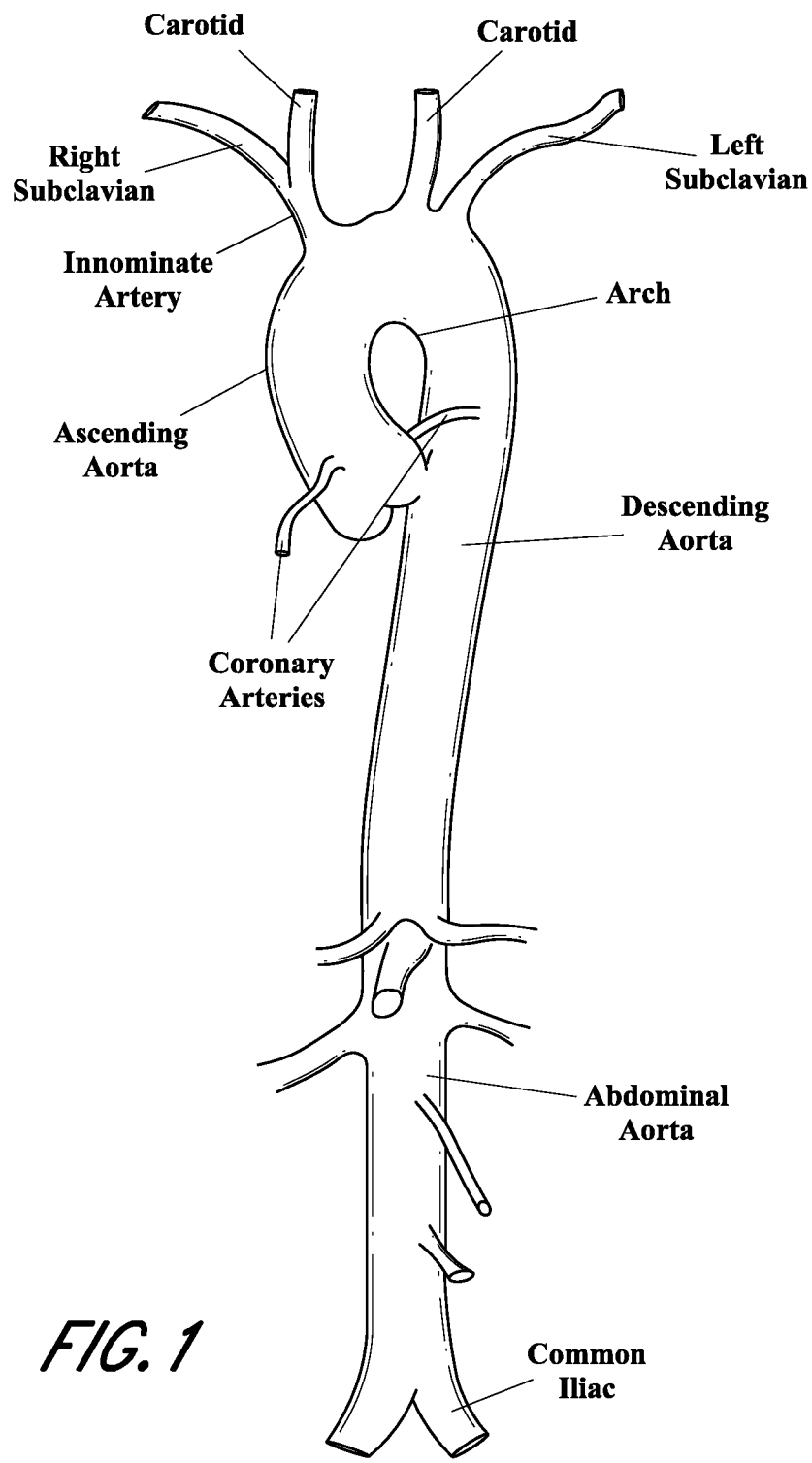
FIG. 1 is a schematic diagram of the central arteries of the human body.

FIG. 1 shows the ascending aorta, which is the portion of the aorta that is directly connected to the heart. The aorta generally extends superiorly in the thorax and curves at the aortic arch to transition to a portion of the aorta that extends inferiorly through the thorax into the abdomen. The ascending aorta is a critical blood vessel segment for several reasons. This segment carries the highest volume of blood of any of the body's arteries. Also, several critical branch arteries extend in this region: coronary arteries extend laterally just outside the heart to supply blood to the heart muscle; carotid arteries extend from the arch region to the brain; and subclavian branches convey blood to the arms. Loss of blood or blockage of these arteries should be avoided in effective treatment of aneurysm or dissection in the ascending and arch regions of the aorta.

A problem with treating the ascending aorta with conventional catheter approaches is a lack of precision in placement of a device. For example, conventional stent-graft catheter platforms are used in the abdominal aorta. This vascular region is less mobile than the ascending aorta.

Figure 1A:
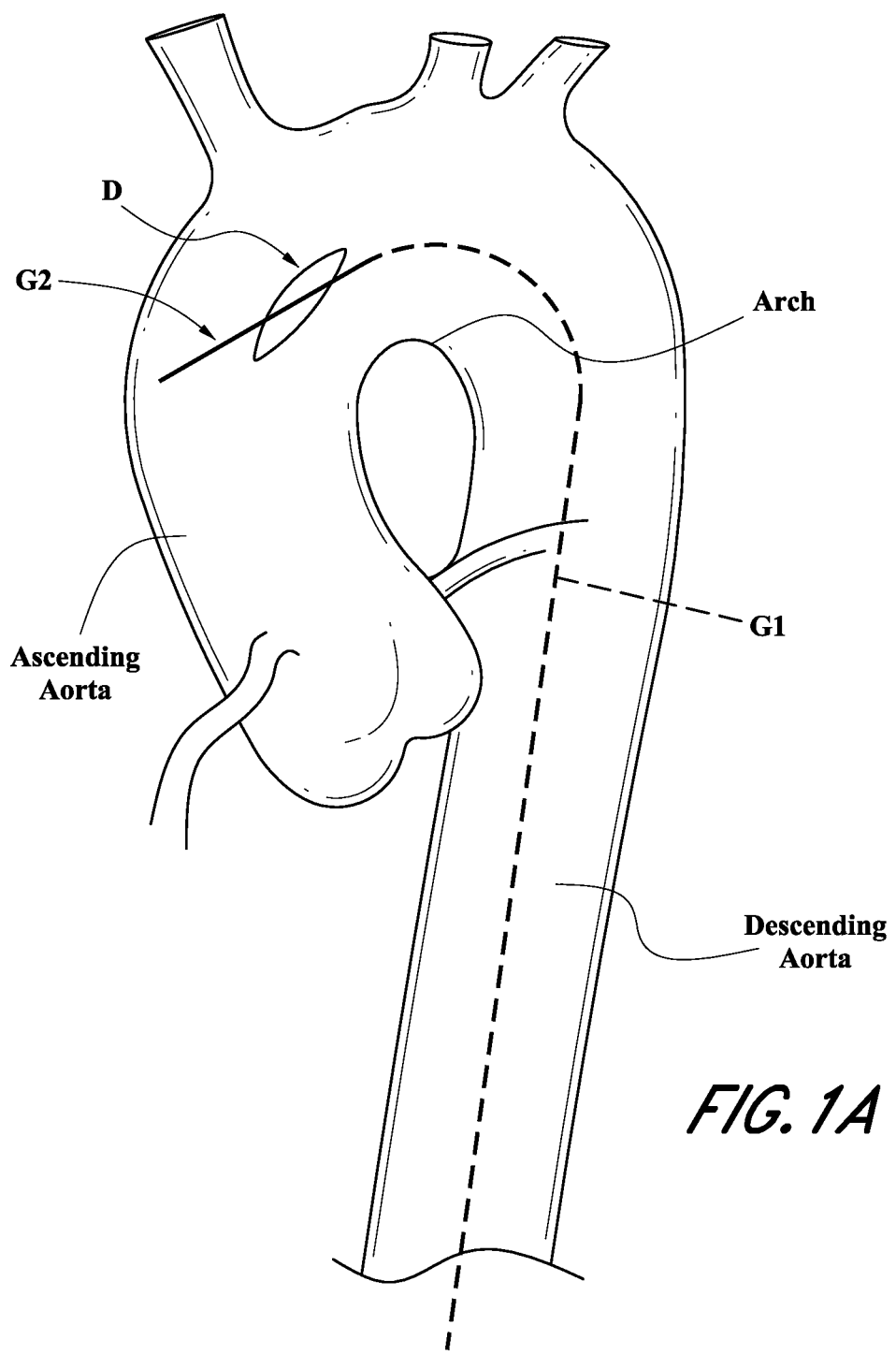
FIG. 1A is a schematic diagram of a dissection in the ascending region of an aorta.

FIG. 1A shows another problem with treating a dissection D using a conventional catheter approach. Typically a guidewire is advanced to the region to be treated. A guidewire could be advanced from a femoral access location to a dissection D located in the ascending aorta. The path of the guidewire for this approach would be over the arch as illustrated by the dashed line G1. Some treatment of dissection involves placing a treatment device at the upstream end of the dissection D. Such placement conventionally requires that the guidewire be advanced past the upstream end of the dissection, i.e., to a location between the heart and the dissection D. FIG. 1A shows that in one complication the guidewire may unfortunately follow the path G2 through the dissection and into the false lumen outside of the wall of the aorta. As a result, the guidewire will guide a catheter device over the arch and through the dissection into the false lumen along the path G2. This can result in the dissection being extended or lengthened at the upstream end of the dissection D. This complication worsens the condition for the patient, is possibly life-threatening, and at minimum makes treatment more difficult.

Although sophisticated imaging technology can help to confirm proper crossing of the dissection D within the lumen of the ascending aorta, it is still possible for the catheter to fail to track the guidewire over the arch but instead to follow the straighter path of G2. This is because the catheter device is generally stiffer than the guidewire and may have tendency to straighten in curved vasculature.

Even if catheter based treatment device can accurately be positioned across the dissection D, accurate placement of the device in the ascending aorta is critical. The ascending aorta extends around and between the aortic valve, coronary arteries ostia, and the supra aortic vessels. Misplacement of a device in this region can lead to complications, such as progressive aortic valve insufficiency and blockage of carotid and/or coronary arteries.

For these reasons, there is need for a stable, well-controlled platform for delivering an implantable device, such as a stent-graft or a dissection treatment device, to the ascending aorta. Such a platform will provide a great advance in treating patients needing repair in this vascular zone. The catheter systems described below provide a stable platform for deploying a device such as a blood vessel graft in such a vessel.

Figure 2:
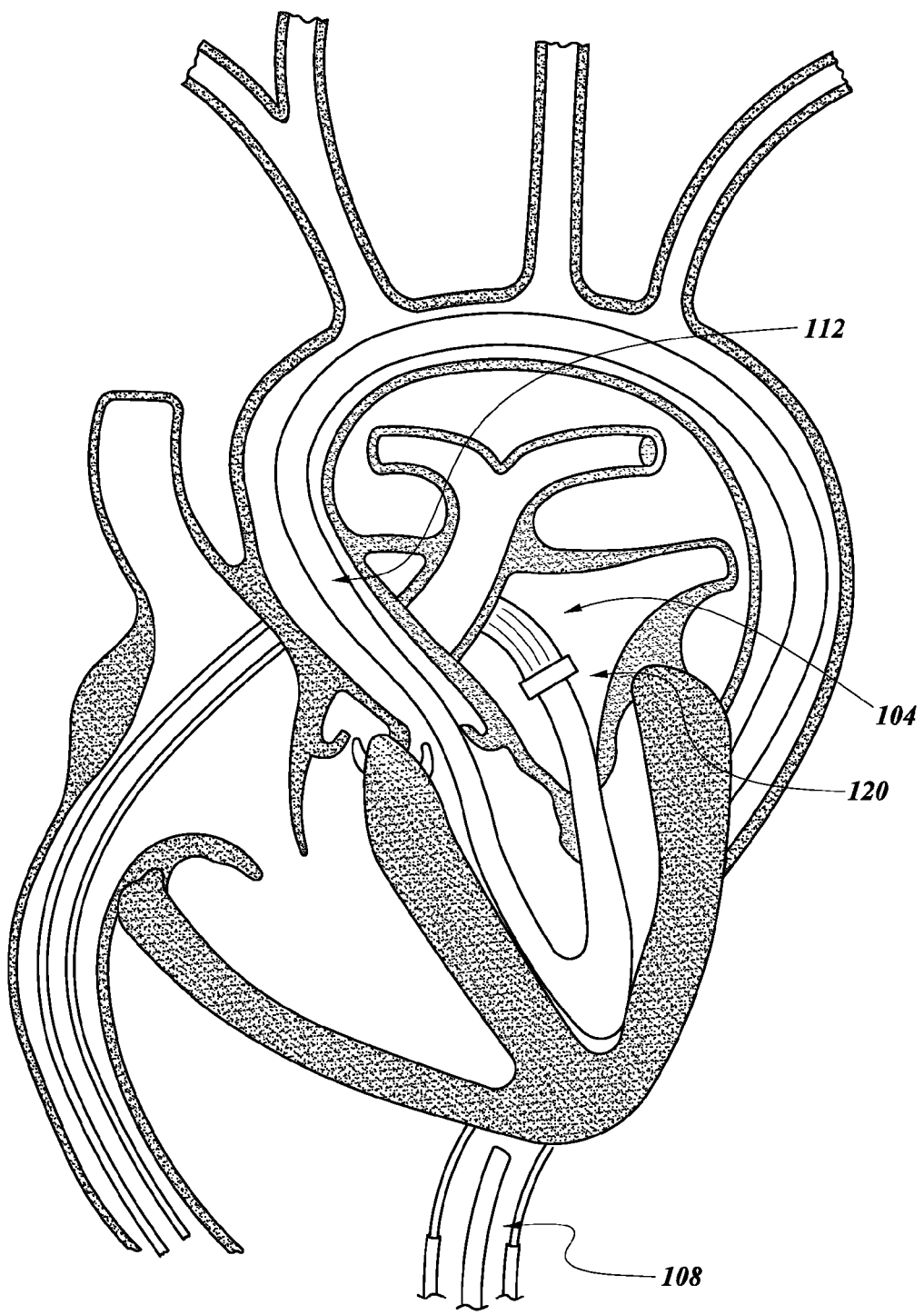
FIG. 2 shows a system and an aspect of a method for treating a patient using a system according to this disclosure.

FIG. 2 shows one embodiment of a system 100 that is adapted for positioning a stent graft in an ascending aorta of a patient. The system 100 has a first catheter 104, a second catheter 108, and a graft deployment zone 112.

The first catheter 104 has a length sufficient to extend from a peripheral venous site to a heart of the patient. The catheter 104 is adapted to be placed across the intra-atrial septum of the heart such that a distal end 120 resides above the mitral valve. In some embodiments and techniques, the distal end 120 can be advanced below the mitral valve, e.g., into the left ventricle. The catheter 104 can have one or several lumens for independent advancement of other devices, such as the second catheter 108 as discussed below.

The second catheter 108 has a length sufficient to extend from the peripheral venous site and through the heart of the patient. FIG. 2 shows that the second catheter 108 may be long enough to extend from adjacent to the heart into more remote regions, for instance to a peripheral arterial site. As discussed more below, the second catheter 108 is advanced in certain methods from the first catheter 104 into the left ventricle and through the left ventricular outflow tract, and into the aorta. Preferably the first catheter 104 is flexible to permit advancement up to and through the atrial septum. The second catheter 108 preferably has another shape or configuration than the first catheter 104 to facilitate passage of a device from the first catheter 10 through the heart. In some embodiments, the second catheter 108 provides a trajectory through the heart anatomy. In various embodiments, the second catheter 108 comprises a dilator for displacing soft tissues, e.g., chordae tendinae, along or adjacent to the trajectory. In various embodiments, the second catheter 108 has a shape that corresponds to an inner cross-section of the ventricle.

A portion of the second catheter 108 is provided with a flexible, bendable section that is able to traverse a bend approaching and in some cases exceeding 180 degrees. The bendable section can be a preformed portion of the second catheter 108. For example, the catheter body can be formed in a way that when at rest and unconstrained the bendable portion of the second catheter 108 has a bend that may conforms to the shape of the anatomy. In some embodiments, the second catheter 108 is constructed with reinforcement, such as with one or a plurality of more rigid structures. Metallic rings or other structures can be provided to yield a preferred shape when the second catheter 108 is in a free state. Another configuration provides a braided structure within the bendable section of the second catheter 108. The braided structure is arranged to bend the bendable section to an appropriate curvature traverse a bend in the heart, e.g., to disposed ventricle contacting portion of a side of the bendable section with opposing walls of the ventricle.

In some embodiments, a preformed introducer aids in progression of the second catheter 108 at various levels. For instance an introducer can be provided that has a first configuration for advancement within the first catheter 104. The introducer can have a second configuration for placing an outlet thereof in the left atrium. The introducer can also have or can be replaced with an introducer that has a third configuration for placing an outlet thereof at or adjacent to the apex of the left ventricle. The second and/or third configurations can provide a distal portion that is shaped according to various angulations. The first configuration can be provided as long as the introducer is disposed within the first catheter 104. The stiffness of the first catheter 104 keeps the introducer straight. When the introducer is advanced out of the distal tip of the first catheter 104, the introducer reverts to the second and/or third configurations. The second and/or third configurations provide that the progression of the second catheter 108 (or a guidewire to guide it) is in the right direction. In one approach, the first and/or second catheters, 104, 108 can then be further advanced, after retrieval of the introducer. The tight bend may also be traversed by the graft deployment zone 112 as discussed further below.

The graft deployment zone 112 can be disposed on the second catheter 108. In other embodiments, the graft deployment zone 112 can be disposed on the first catheter 104, the second catheter 108, or partly on first and partly on the second catheter. In one variation, the second catheter 108 comprises an assembly including a sheath and an inner body. The sheath can be disposed between the inner body and the first catheter 104 in some portions of the device or during some phases of a procedure.

The system 100 also can include an implantable device configured to treat a malady in the vasculature. The system 100 is well adapted for heart adjacent vessels, and in particular for blood vessels that may require high angle bends, short radius bends, or a combination of high angle and short radius bends. The implantable device can include self-expanding anchors that may be held between the first and second catheters 104, 108.

In some embodiments, the system 100 includes a rail that extends from the heart to at least one of a peripheral venous and an arterial site. In one embodiment, a rail can extend from the first catheter 104 to the arterial site. The rail can be an elongate body that is accessible to the clinician for advancing devices with or against flow in the arterial side to the treatment site. For instance after the rail is placed, an elongate body can be advanced over the rail from within the first catheter 104 to the ascending aorta.

Figure 3:
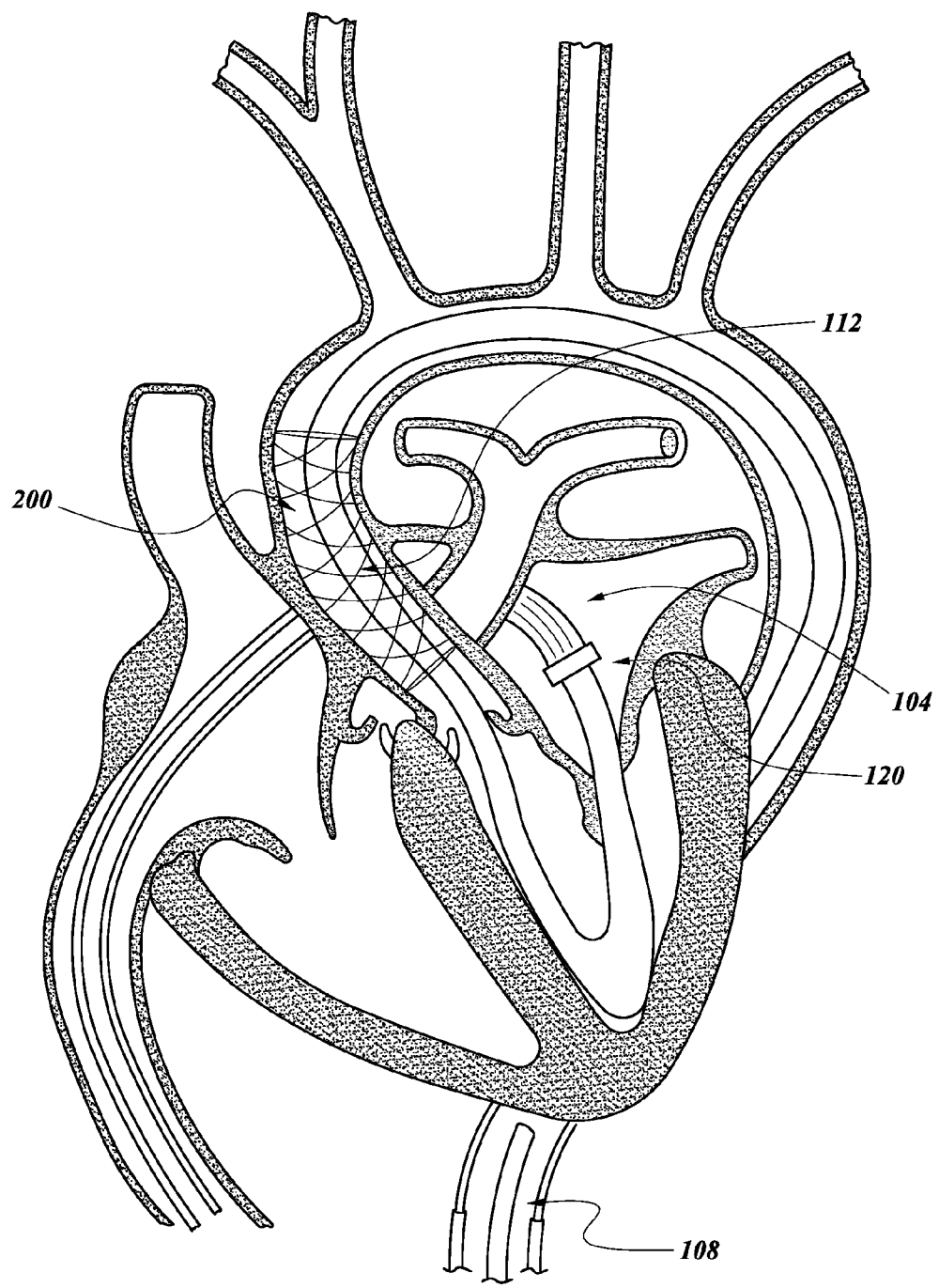
FIG. 3 shows a deployed device in the ascending aorta, the device being deployed from a deployment zone of the system of FIG. 2.

A graft device 200, e.g., a stent-graft as shown in an expanded state in FIG. 3, is an example of an implantable device. Features of the graft device 200 that make it more expandable under these circumstances include providing a stent-like structure with struts or circumferential members and an open cell structure. In the case of dissection, depending on the location of the tear in the ascending aorta, different sorts of graft devices may be used. As reported in Lu, Q. et al., *Endovascular Repair of Ascending Aortic Dissections*, JACC Vol. 61, No. 18 1917, 1922 one approach is to place a branched endograft in a distal region of the ascending aorta. This device is an example of a device that can maintain perfusion into the brachial cephalic blood vessels. Other examples include hybrid or fenestrated designs. For tears in a middle portion, e.g., a middle one-third of the ascending aorta, the graft device 200 may include a straight single lumen structure, such as a graft, supported by stents or other similar supports. In one variation, the graft device 200 is supported by a bare metal stent at a distal zone (away from the heart). A proximal portion of the graft device 200 preferably is supported by a structure that will not irritate the aortic valve or occlude the coronary arteries. In various embodiments, the proximal portion of the graft device 200 includes a stent, e.g., a bare metal stent.

The graft device 200 can be approximately 100 mm or less in length, e.g., to enable placement proximate the innominate artery. Grafts with a length of between about 75 mm and about 85 mm could be used in some techniques. More generally, for dissection, the length of the graft 200 can be just long enough to cover the proximal (upstream) portion or region of the tear. This is considered sufficient treatment for certain forms of dissection. The graft device 200 can be longer than 100 mm, e.g., in techniques where patency of supra-aortic vessels is provided by other techniques. For example, a path can be provided by fenestrations or branches in the graft device 200 or by a bypass graft. The graft device 200 can have a width, e.g., diameter, of approximately 46 mm or more. Smaller grafts could also be used in some techniques, e.g., with a width (e.g., diameter) between about 32 and about 42 mm.

FIG. 3 shows that at least a portion of the system 100 can remain in place shortly after the graft device 200 (or other device) is placed in the patient. The system 100 can include components that can be removed from the peripheral arterial site, the peripheral venous site, or from the peripheral arterial and venous sites simultaneously. Simultaneous removal can be accomplished by enabling at least one of the catheters 104, 108 to be separated into two or more sections.

The system 100 can enable various advantageous methods of treating a patient with at-risk sections of the aorta. In one method, the graft device 200 is positioned in an ascending aorta of a patient. At one stage of the method, a peripheral venous site is accessed. Such access can be in a standard manner, using a plurality of progressively larger cannulae and optionally an access sheath. Thereafter, the catheter 100 is advanced through the peripheral venous site through a portion of the vena cava into the right atrium of the patient. Thereafter, access is provided to the leaf atrium across an intra-atrial septum. In one embodiment, the catheter 104 is advanced through the septum to a left atrium of a patient. FIG. 2 illustrates a later stage, in which the second catheter 108 is advanced distally from the first catheter 104.

The second catheter 108 is advanced through the left ventricle and, in some embodiments, into the aorta. Any technique for traversing this path can be taken. For instance, a flow directed catheter or guide device can be released from the first catheter 104 into the blood flow. Aspects of this approach are discussed below in connection with FIG. 6. The flow directed catheter or guide device can follow the flow of blood through the chordae tendinae, the left ventricle outflow tract and across the aortic valve. The second catheter 108 can follow the flow directed catheter or guide device across the aortic valve and into the ascending aorta. The flow directed catheter can be integrated into the second catheter 108 in some embodiments.

Figure 4:
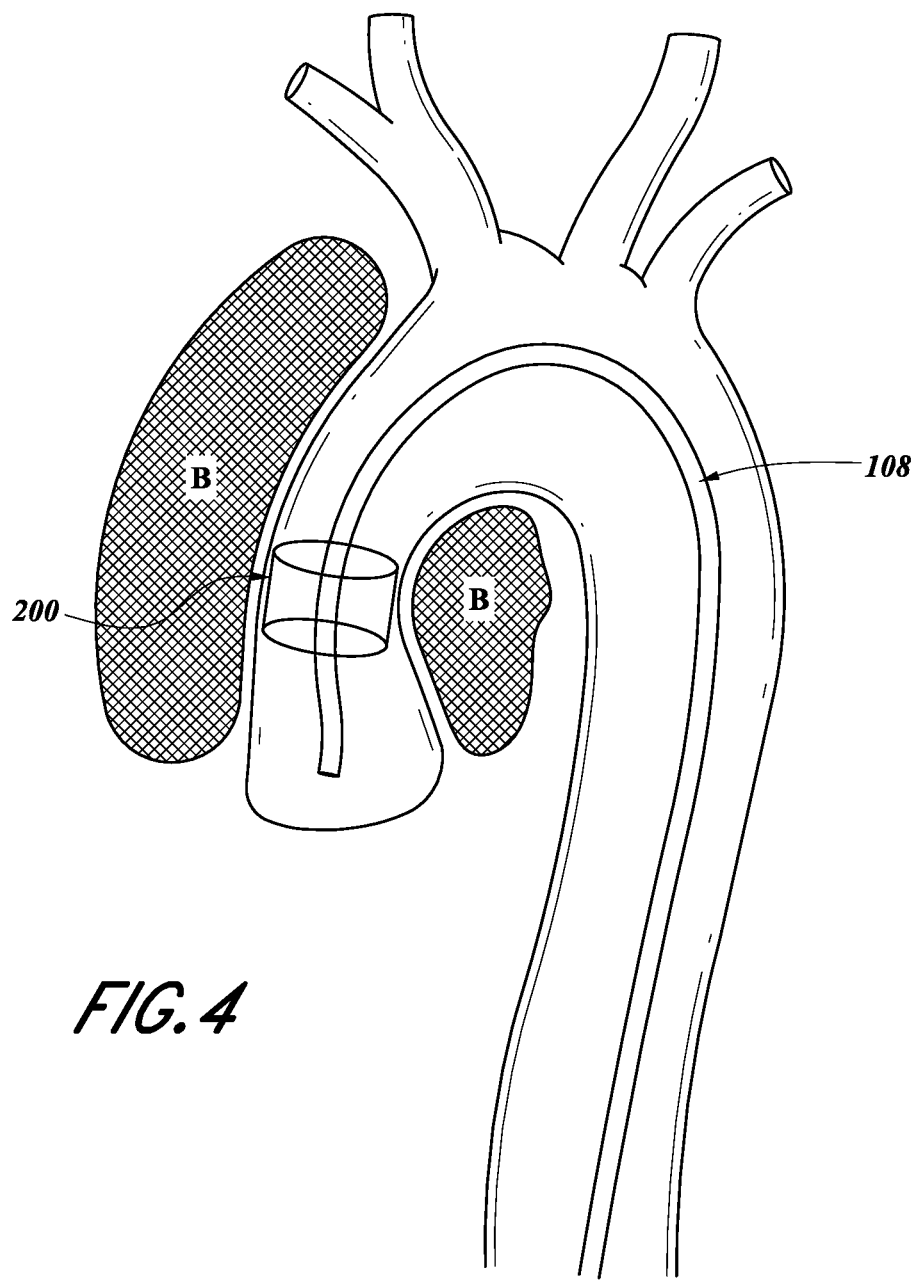
FIG. 4 illustrates placement of a graft device in a patient suffering from a Type II (De Bakey classification) dissection of the ascending aorta.
Figure 5:
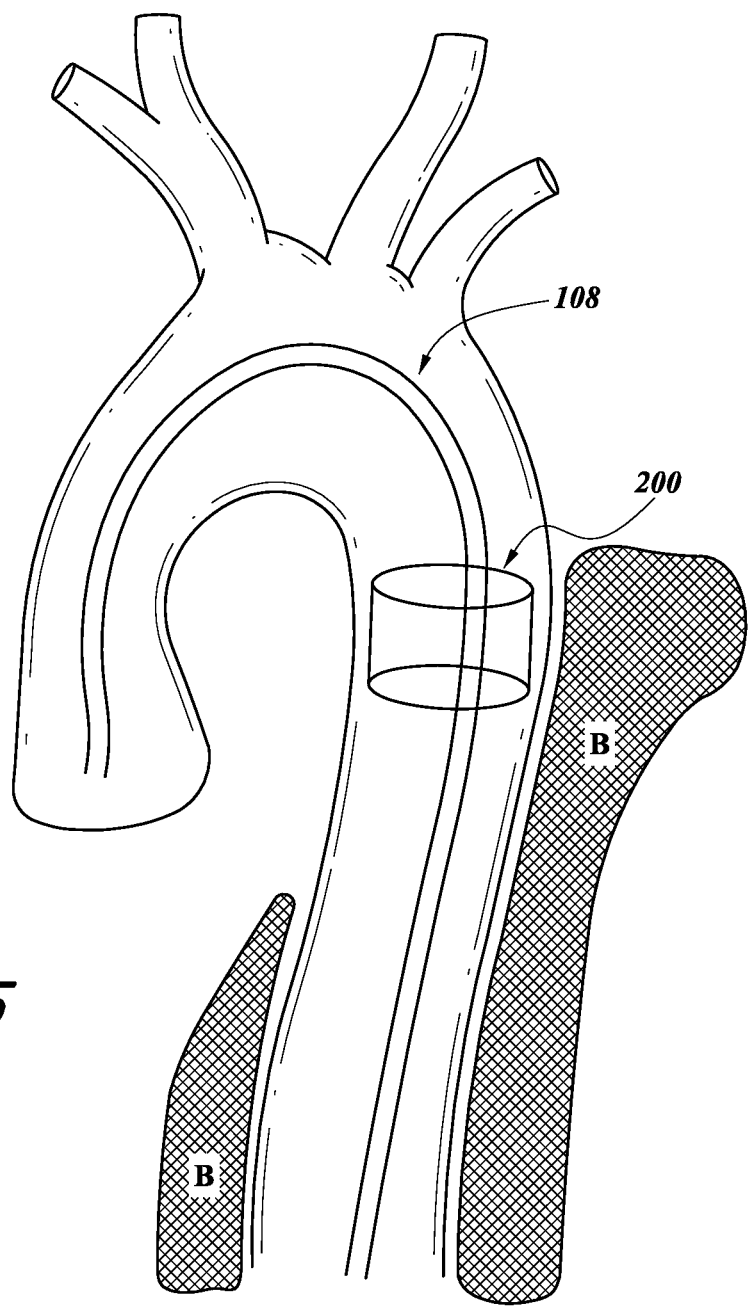
FIG. 5 illustrates placement of a graft device in a patient suffering from a Type III (De Bakey classification) dissection of the descending aorta.

The graft device 200 is advanced from a peripheral site to the treatment site. In one technique, the graft device 200 is advanced from the venous site to the treatment site until the graft device 200 reaches an ascending aorta of the patient. This is a particularly advantageous and safer than a conventional approach for aortic dissections, whether Type I or II (De Bakey classification) dissection (as collectively illustrated by the shaded regions B in FIG. 4) or Type III (De Bakey classification) dissection (as shown by the shaded regions B in FIG. 5). As discussed in FIG. 1A, in a conventional approach, a free end of a catheter is advanced up the aorta from, and over the aortic arch into the descending aorta. Although the catheter may be tracking a guidewire, because the wire is generally less stiff than the catheter and the vasculature has significant non-linearity the free end of the catheter may not track well. This approach will initially cross the distal (downstream) end of the dissection, and will have to cross the length of the tear to beyond the proximal end thereof. These factors create a heightened risk of directing the free end of the catheter into the false lumen formed by the dissection, i.e., along the path G2 in FIG. 1A.

Techniques according to this application enable the catheter 108 to traverse the aortic valve and thereafter follow a portion of the true lumen of aorta. Many therapies only require treating the end of a tear that is closer to the heart. So, with reference to FIG. 1A, the catheter 108 need not be advanced along the entire length of the dissection D to the distal (downstream) end thereof to a location where it could pass into the false lumen to extend the aortic dissection. For instance, the catheter 108 can be kept proximal of the distal end of the tear if the tear is elongate.

In one technique the graft device 200 is disposed on or in the second catheter 108 and is initially advanced with it. The graft device 200 is positioned at a treatment site within the ascending aorta. As noted above, in the case of dissection, the treatment site may be primarily or entirely at the end of the tear closest to the heart. In some cases, the catheter 108 is kept proximal of the distal end of the dissection or tear. In a first technique, the graft device 200 is disposed between an inner body of the catheter 108 and an outer body of the second catheter 108. The outer body is moved relative to the inner body to release the graft device 200. In one embodiment, the graft device 200 includes a sleeve member and one or more supports. The sleeve material preferably is a material that is biocompatible, such as Dacron, or ePTFE or the like, and may be configured to permit endothelialization or other mechanism of ingrowth of vascular tissue or cells within or on the sleeve. The advancement from the venous site is facilitated by making the sleeve and supports capable of traversing large angle bends, a tight radius, and in some cases both large angle bends and tight radii.

The support(s) of the device 200 can be self-expanding upon being uncovered by movement of the outer body. The supports can be stent-like constructs that have at least two configurations, e.g., a low profile configuration for delivery and a higher profile configuration for holding an aneurysm covering device, such as the sleeve, in place. The supports can be permanent, biodegradable, or partially biodegradable. In some cases, the supports can be coated with a drug. The drug can be any vascular pharmaceutical agent configured to have a beneficial effect, including without limitation anti-inflation effect, anti stenotic effect, anti-thrombotic effect, and other beneficial effect. In another variant, the sleeve and/or the supports of the graft device 200 can be mounted on a balloon. After the graft device 200 is positioned at the treatment site the balloon is expanded to enlarge the sleeve and/or the supports to a grafting configuration from a lower profile delivery configuration.

In another technique, a rail is established in the vasculature from the venous side, through the heart and to a remote arterial site. In these embodiments, the graft device 200 can be safely advanced from the arterial site to the treatment site in a region of the ascending aorta. For aneurysm treatment, this approach may be more straight-forward than advancing the device 200 from the venous side, through the heart, to the treatment site in that fewer sharp tight corner bends are required. However, the stable rail configuration improves the precision of placement over conventional techniques, discussed above. Even for treating dissection, the rail based arterial approach would be much safer than merely advancing over a guidewire as is conventional, whether Type I, II, or III because the rail (e.g., as formed by the catheters 104, 108) more stably guides and positions the structure upon which the graft device 200 is mounted.

In one technique the graft device 200 is disposed on or in a catheter body that can be advanced from the arterial peripheral site against flow through the aorta toward the heart. The graft device 200 is positioned at a treatment site within the ascending aorta. The graft device 200 can include a sleeve and support and can be configured to be advanced over the rail, which can be formed by the first and second catheters 104, 108. Placement of the arterially delivered graft device 200 can be by withdrawing a catheter body to expose a self-expanding support. Placement of the arterially delivered graft device 200 can be by expanding a balloon upon which the graft device or portion thereof is mounted. The graft device for arterial delivery can include a sleeve and supports as discussed above.

Another advantage of the systems and approaches described herein is that the likelihood of an inadvertent extension of a dissection due to a device being extended into a false lumen is reduced or eliminated. For example, as discussed above, a rail can be established by passing the catheter 108 through the heart into the aorta, to the arterial access site. This can be done with a small low stiffness device such as a flow directed catheter initially. The rail (e.g., including the catheter 108) can track the flow directed catheter to the arterial site, e.g., to the femoral artery. Once the rail is established, a delivery system for the graft device 200 can track over the rail without risk of inadvertently being advanced into the false lumen disposed around the blood vessel. This reduces the risk of extending the tear of the aorta. Use of the rail can allow the graft device 200 to be delivered through the heart chambers and the aortic valve to the ascending aorta in other techniques. In some cases, the use of the rail can allow the graft device 200 to be delivered up the descending aorta and over the arch in one technique.

FIGS. 6-10 illustrate variations of a catheter system 300 for treating dissections and aneurysms in the ascending section and other portions of the aorta. The system 300 includes a first catheter body 304 and a second catheter body 308. The first and second catheter bodies 304, 308 can be positioned separately but operate together to facilitate a stable platform from which vascular devices can be deployed.

The first catheter body 304 preferably has an elongate structure 312 that is configured to be advanced from a peripheral access site, such as a femoral vein, through the inferior vena cava and into the heart in a manner similar to that discussed above. A distal portion 316 of the elongate structure 312 preferably is configured to extend across the atrial septum of the heart and through the mitral valve. The distal portion 316 preferably is further configured to be disposed in the ventricle adjacent to the apex of the heart. In one embodiment, the distal portion 316 has a tip section 320 that is preformed or deflectable to be oriented toward the left ventricle outflow tract (LVOT). The tip section 320 can be pre-formed to present a tracking device release or capturing platform that is well oriented for creating a stable transvalvular rail. In some embodiments, the tip section 320 is pre-formed to provide a reliable and predictable position of a tracking device opening upon being released inside the heart. For instance, a first portion of a lateral edge of the tip section 320 extend out of the first catheter body 304 and can thereafter curve toward a first wall of the left ventricle, a second portion of the lateral edge distal the first portion of the tip section 320 can curve about, above, or on the inside of the left ventricular apex, and a third portion of the lateral edge of the tip section 320 can curve away from the second portion. This structure enables the third portion of the lateral edge of the tip section 320 to stand off of the wall of the heart when the tip section is deployed. By carefully inducing the curves at the first, second and third portions of the tip section 320, an opening at the end of the tip section 320 can be properly positioned and oriented relative to the aortic valves, as discussed elsewhere herein. The curvature of the tip section 320 can be crated in any suitable way, such as by temporarily heating the tip section, curving and holding the tip section in the desired shape when heated and/or when cooling. In some embodiments, custom reinforcement can be provided that induce an anatomy appropriate shape of the tip section 320. Reinforcement may be by inclusion of metallic rings or other similar rigid members. Another option is to use a pre-shaped introducer (as discussed above), to pass a wire, and insert a catheter that is not pre-formed that will follow the path (and shape) of the guidewire. The shaped guidewire may be configured to follow the anatomy of the inside of the ventricle, into the left ventricular outflow track. In this position and orientation an orifice 324, which can be a distal opening of the tip section 320, faces up the LVOT. In some embodiments, when so placed the plane of the orifice 324 is aligned with, e.g., substantially parallel to a plane including the opening formed when the aortic valve is open. In this context, substantially parallel means that an angle of less than 20 degrees is formed between the plane of the orifice 324 and the aortic valve. This alignment is not required, but where provided is advantageous in that a direct path is provided from the orifice 324 through the valve.

Figure 6:
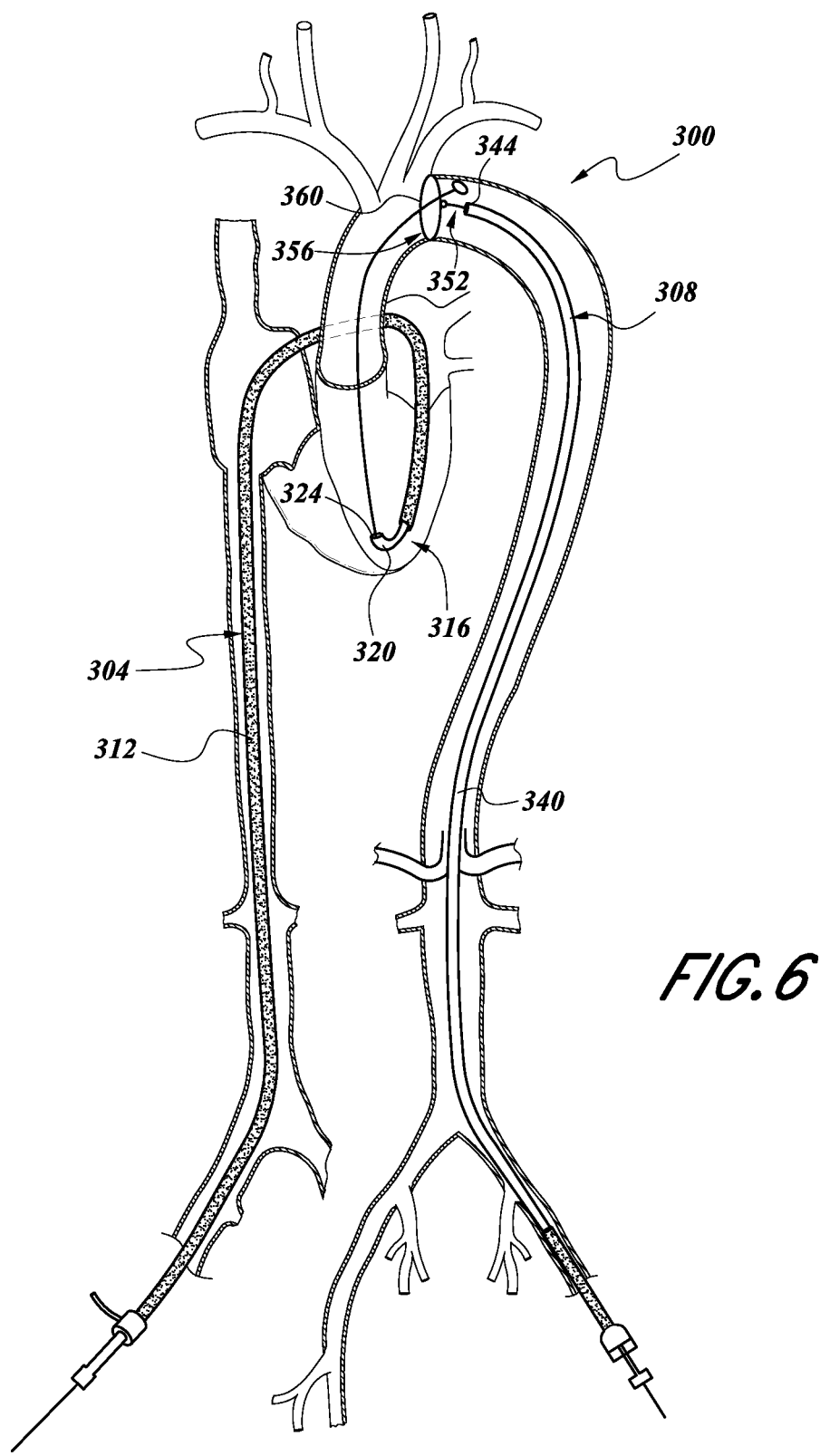
FIG. 6 illustrates another system and an aspect of a method for providing a stable platform for deployment of a vascular device.

FIG. 6 also illustrates a system and method for facilitating connection of the first and second catheter bodies 304, 308. In particular, the second catheter body 308 has an elongate structure 340 that is configured to be advanced from a peripheral access site, such as a femoral artery, through the aorta. In the illustrated technique a tip section 344 of the second catheter body 308 is positioned in the aortic arch. A connection between the first and second catheter bodies 304, 308 can be made by use of a flow directed device 352 and a snare 356. The flow directed device 352 can have a balloon disposed at a distal end thereof. The balloon is released from the orifice 324 into the ventricle. Blood flow in the beating heart carries the flow directed device 352 out of the heart into the aorta as shown in FIG. 6. The snare 356 is advanced out of the second catheter body 308 and expanded to permit the flow directed device 352 to pass therethrough.

In one embodiment, the snare 356 includes a loop 360 that can be expanded or unfurled in the aorta into a position close to, e.g., apposing, the walls of the aorta. The loop 360 is connected to an elongate body 364 that is passed through the second catheter body 308. The snare 356 can be coupled with the flow directed device 352 and can be urged proximally within the second catheter body 308 to draw the flow directed device 352 through the distal end of the second catheter body 308.

Preferably the flow directed device 352 is connected to an elongate body 368 that extends within the first catheter body 304 and that is sufficiently long to extend from the peripheral venous site to the peripheral arterial site. The elongate body 368 is coupled with the flow directed device 352 acts as a guide member for accurately guiding the distal end of the second catheter body 308 into close position with the distal end of the first catheter body 304 as shown in the inset image of FIG. 9.

Figure 7:
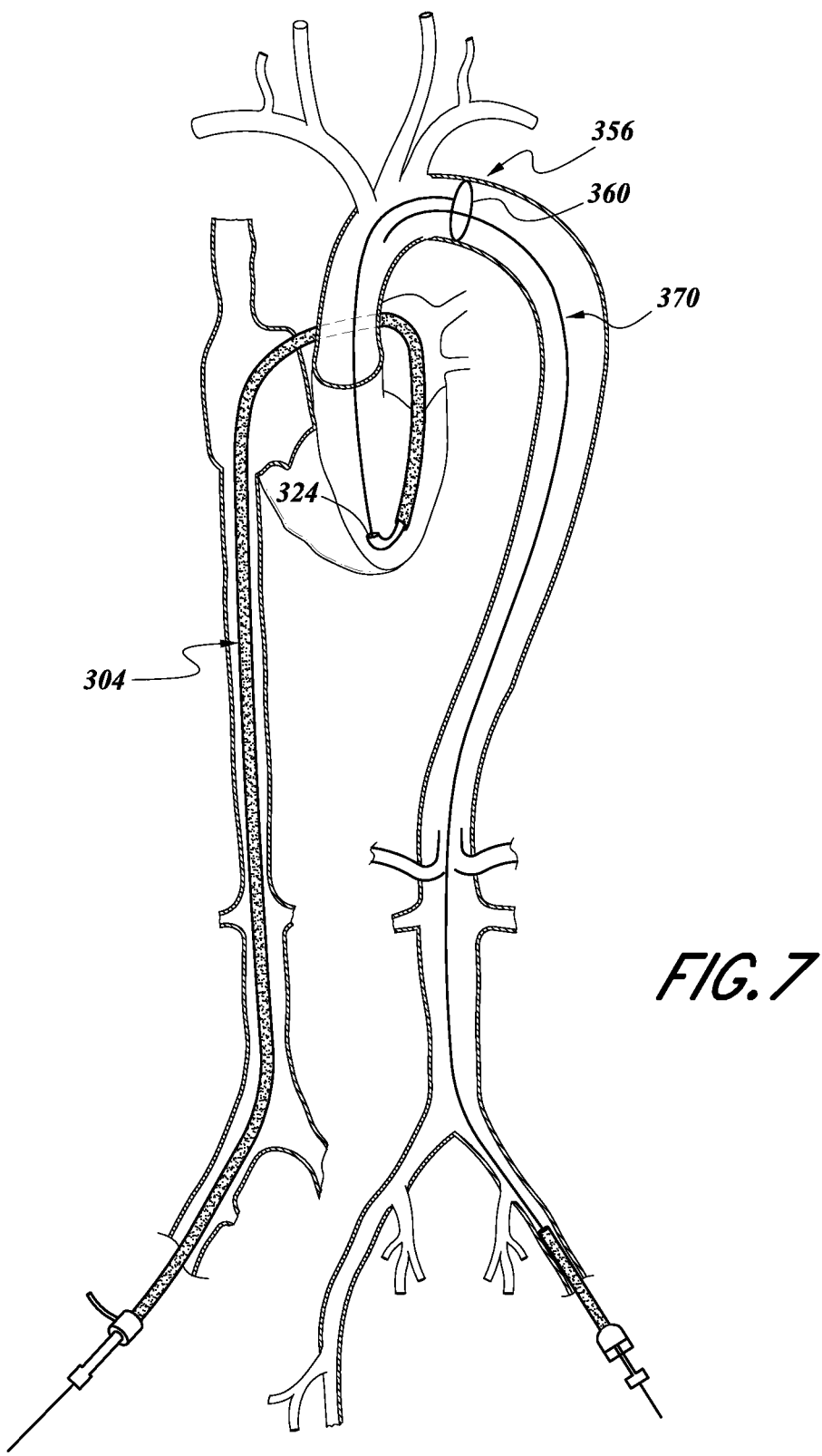
FIG. 7 illustrates a variation of the aspect of the method illustrated in FIG. 6.

FIG. 7 shows an alternative method where a snare is operated from the venous side. In this approach, the first catheter body 304 is placed in the same position as illustrated in FIG. 6. Thereafter, a guidewire 370 is advanced into a peripheral artery, such as a femoral artery as shown in FIG. 7. The guidewire 370 may have a distal segment that is shaped to facilitate snaring by another device, as discussed below. The snare 356 can be advanced through the first catheter body 304 as shown in FIG. 6. This approach may be more challenging in that the snare 356 must cross the aortic valve prior to being positioned around the guidewire 370. If needed, imaging technology can be used to confirm proper positioning of the snare 356 and the guidewire 370. For instance, fluoroscopy, and/or ultrasound can be used. Specific imaging approaches from which images may be gathered include transthoracic, transesophageal, intracardiac and/or intravascular imaging approaches. Two dimensional and three dimensional imaging produced from various techniques, including ultrasound, echocardiography, CT scans, and/or MRI, can be used.

After being snared, the guidewire 370 can be drawn by the snare 356 into the first catheter body 304 through the orifice 324 and pulled through the proximal end of the first catheter body 304. Thereafter the tip section 344 of the second catheter body 308 can be advanced over the guidewire 370 over the aortic arch, across the aortic valve and into close position with the tip section 320 of the first catheter body 304.

Figures 9, 9A:
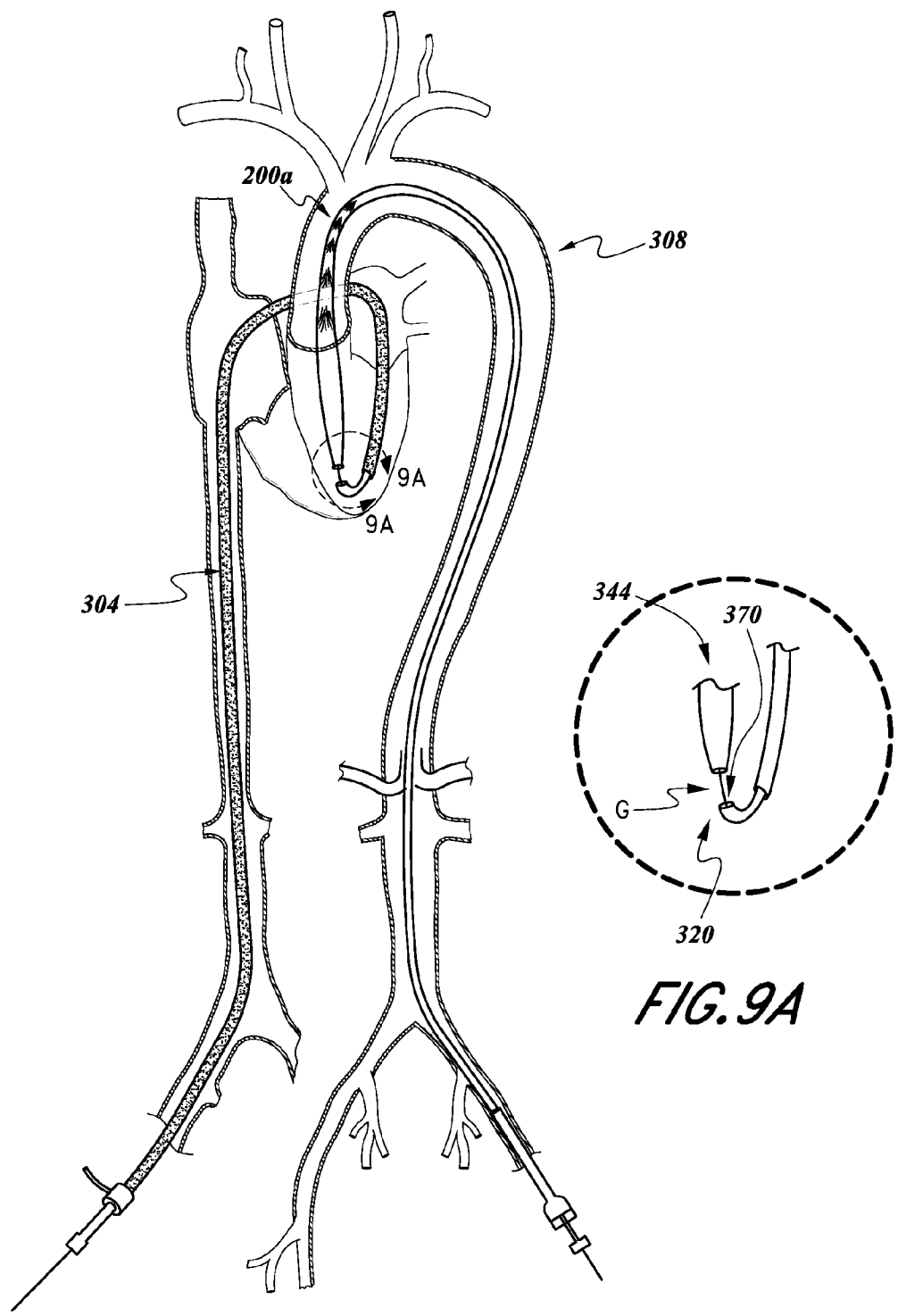
FIG. 9 illustrates another system and a method step subsequent to that of FIG. 8, during which a vascular prosthesis is deployed.
FIG. 9A is a detail view of a portion of the system of FIG. 9 as used in the method illustrated.

FIG. 9 illustrates further techniques that may be employed with the system 300 to deploy a stent-graft or other vascular device. In one approach, the guidewire 370 remains in place to unify the catheter bodies 304, 308. The inset image shows a small gap G between the tip sections 320, 344. The guidewire 370 can be seen to bridge the gap G. In one technique the catheter body 308 includes an inner body and an outer body. A graft deployment zone is defined between the inner and outer bodies. The inner body can be held stationary while the outer body is withdrawn to expose a portion of the deployment zone where the stent graft 200A is positioned. The stent graft 200A can be self-expanding such that by exposing its outer surface, the stent-graft 200A will automatically expand into apposition with the ascending aorta. An advantage of maintaining the gap G even as the stent-graft 200A (or other vascular device) is being placed is that the catheter bodies 304, 308 are allowed to move a small amount relative to each other, e.g., at the tip sections 320, 344. By preserving such relative motion, the catheter system 300 retains more flexibility while still providing sufficient control upon release of the stent-graft 200A (or other vascular device).

Figure 8:
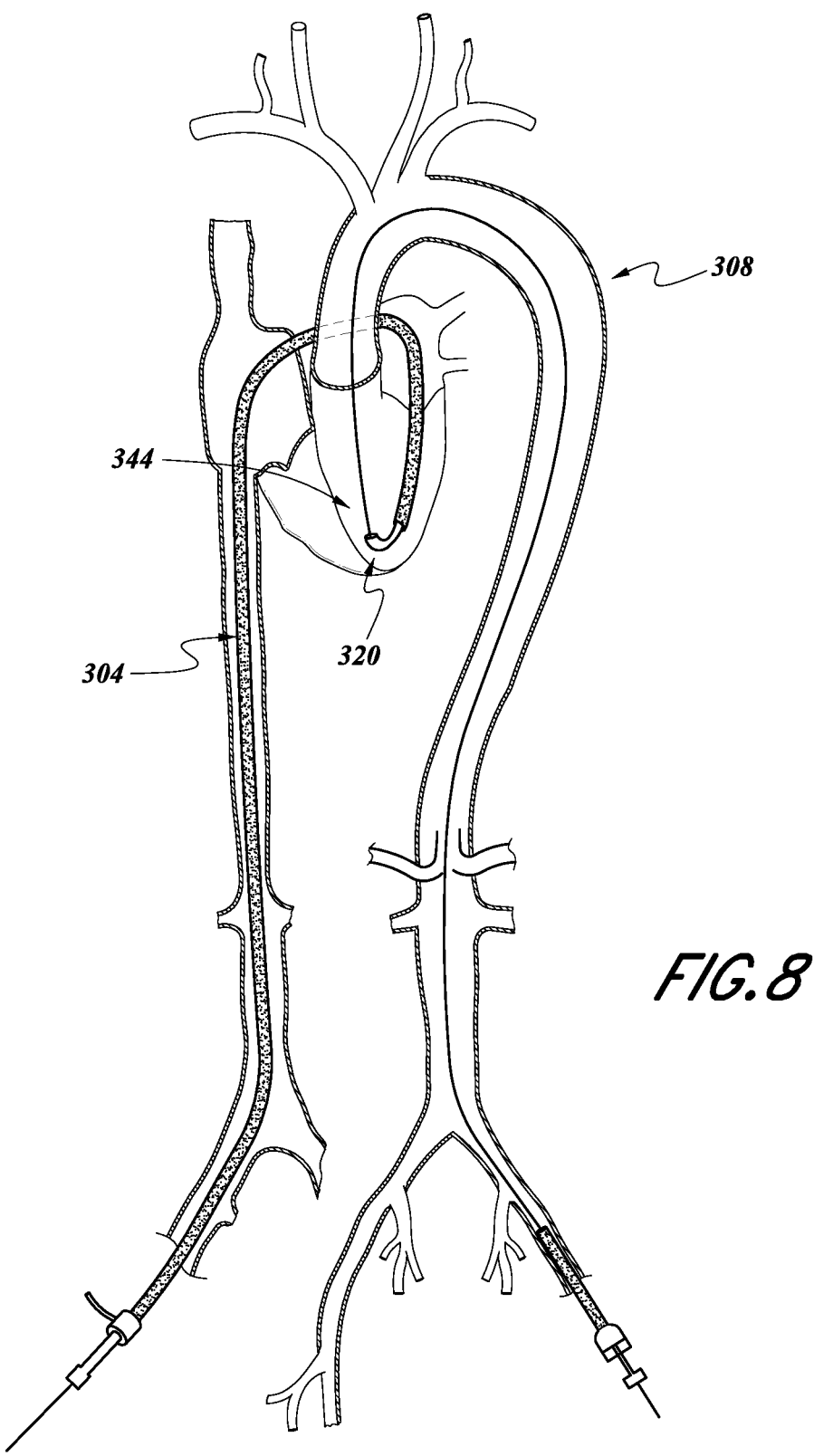
FIG. 8 illustrates another system and a method step subsequent to the method step of FIG. 6.

A variant of the system illustrated by FIG. 8 includes a coupling device or structure whereby the tip sections 320, 344 can be joined together. Any suitable technique for joining these sections can be used. For instance, a threaded connection could be provided between the tip sections 320, 344. In one embodiment case, tip section 320 has external threads and tip section 344 has internal threads. In another embodiment case, tip section 344 has external threads and tip section 320 has internal threads.

While threads are a simple connection structure, it may be preferable to minimize the maneuver to connect the tip sections 320, 344. In one example, a slot is provided that extends proximally within one of the tip sections 320, 344. The slot can have a portion that extends longitudinally parallel to the longitudinal axis of the corresponding tip section. The slot also can have a portion that extends transverse to the longitudinally extending portion. In one embodiment, the slot has a J-shaped configuration. A protrusion can be provided on the other of the tip sections 324, 344. The protrusion is configured to slide along the slot from an open end to a captured position in which the tip sections 320, 344 are joined so that they operate together as a unit.

An advantage of providing threads, the slot/protrusion joint or other unitizing connection is that even more stability can be provided at the tip sections 320, 344, at the deployment zone 312 or at both of these locations. More stability enhances precision of placement of the vascular device. Precise placement can be important to treating certain maladies. For instance, it may be sufficient to treat a vascular dissection at an upstream end, e.g., an end closest to the heart. It may at the same time be preferable not to place a vascular device in a location where it is not needed or may cause irritation, e.g., too close to the aortic valve or ostia into the coronary arteries. Thus, the more stable system enables more targeted treatment that is safer during the procedure, e.g., minimizing the chance of extending the dissection, and also afterward, e.g., minimizing misplacement or covering anatomy that should not or need not be covered.

Figure 10:
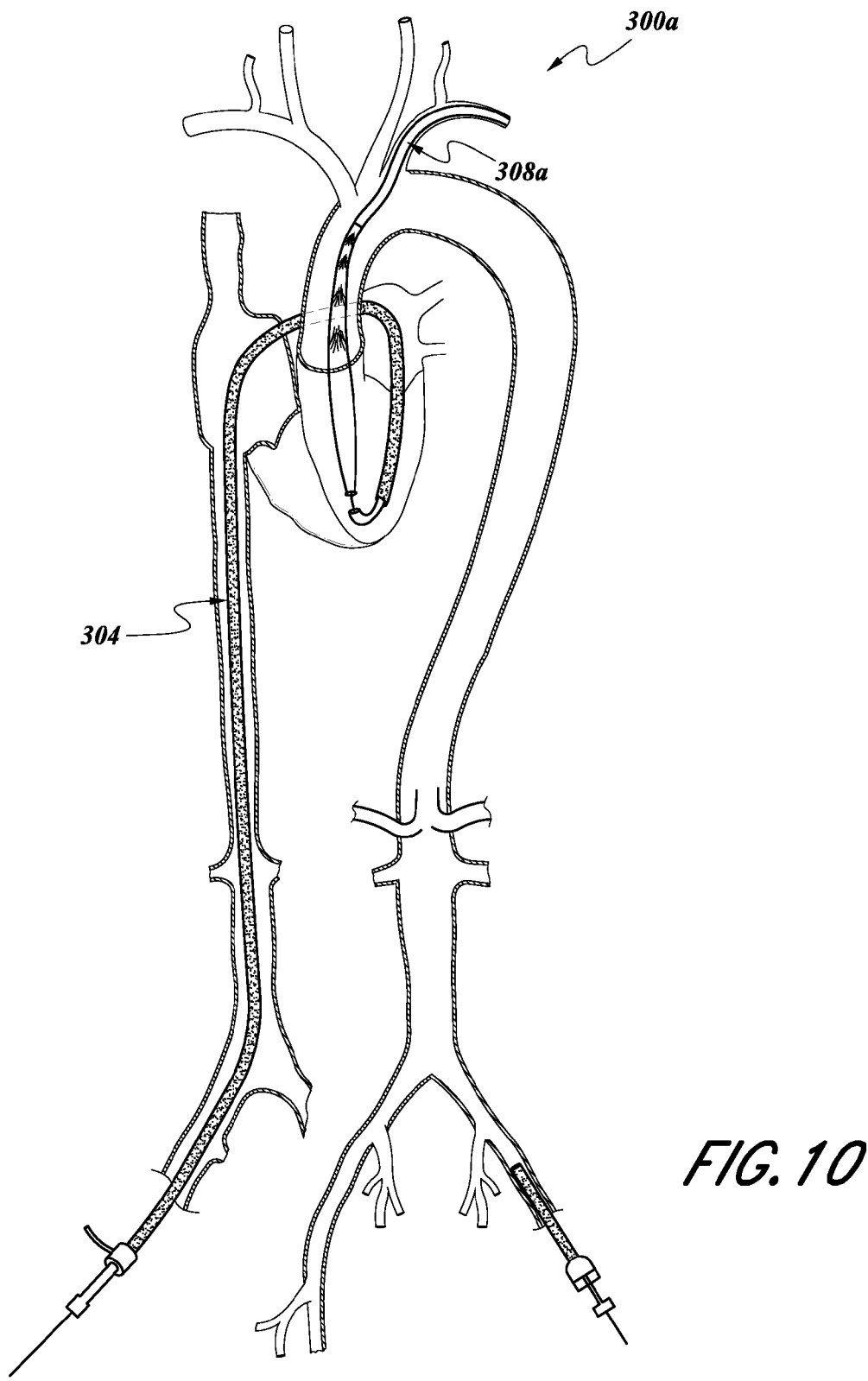
FIG. 10 illustrates an alternative approach to that of FIG. 8.

FIG. 10 illustrates an alternative system 400 and approach that can be applied through a peripheral blood vessel other than the femoral artery. For example, the subclavian artery, the common carotid artery, or the brachial artery in the arm can be used to provide arterial access. The catheter body 308A can be advanced through this site into the aorta using any of the techniques noted above. In case of miniaturization of devices, a radial approach could be used, as seen in coronary catheterization. These approaches reduce the number of angulations and allow better tracking of delivery systems than the femoral approach. They may also reduce complications associated with femoral access and enable patients to more quickly leave the health care facility and recover.

FIG. 10A shows a system and a late stage of a method that can be included with any of the embodiments herein that involves extending devices across the atrial septum. In particular, a septal closure system 400 can be provided and can be advanced up to the atrial septum A. One system includes a catheter 404 that can be advanced into the vasculature and through the vena cava into the right atrium. The catheter 404 can have a closure device 408 disposed adjacent to a distal end thereof. The closure device 408 can have any suitable configuration, e.g., can be expandable. In one embodiment, the closure device 408 comprises a right atrial portion 412A and a left atrial portion 412B. A medial portion 412C can be configured to traverse the thickness of the atrial wall. A seal is provided when the medial portion 412C is disposed in the atrial wall and the right and left atrial portions 412A, 412B are in apposition with the atrial septum A.

Figure 11:
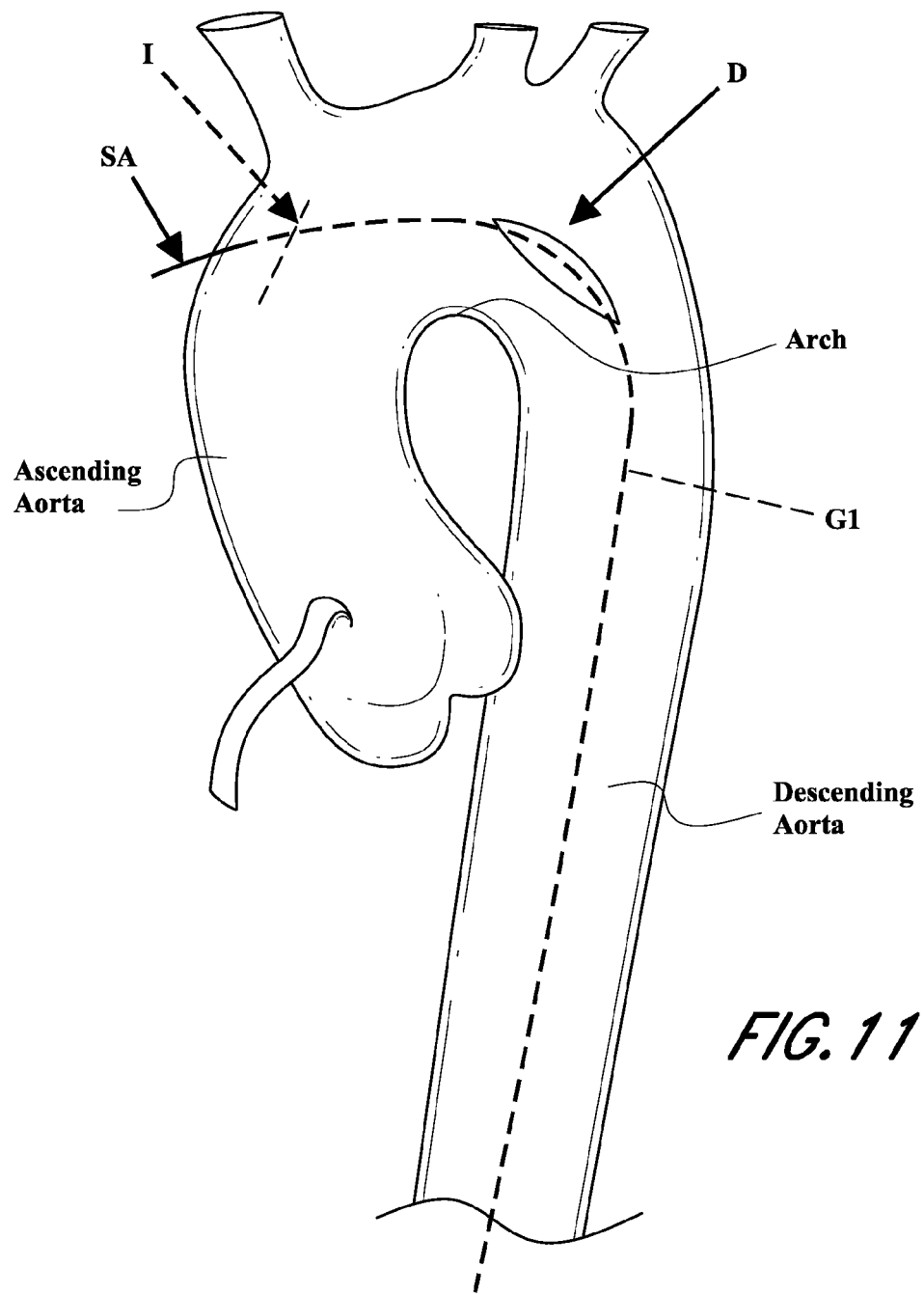
FIG. 11 illustrates a surgical approach involving accessing the vasculature through an incision in the distal ascending aorta.

FIG. 11 illustrates another technique that could be used in combination with devices and techniques discussed above to provide a safe approach to a dissection, aneurysm or other malady. FIG. 11 shows a Type III dissection D. As discussed above, one complication that is to be avoided is inadvertent extension or elongation of the dissection D by advancing a stiff device into the false lumen around the aorta at the dissection. This can be avoided by creating a stable rail or track from a surgical access SA device or path through an incision I made upstream of the dissection D to a peripheral site downstream of the dissection D. For example, the incision I can be made in the distal ascending aorta as shown. One skilled in the art will note that the location of the incision I can be accessed by a sternotomy procedure (e.g., an access to ascending aorta and/or arch). The location of the dissection D in FIG. 11 will not be accessible through the sternotomy procedure and will be less invasively treated using the methods described herein. After the incision I is made, an introducer or other port device can be placed at SA through the incision I to a position where an opening the introducer is inside the aorta. Examples of surgical access of this sort can be found in U.S. Pat. No. 7,488,344, which is hereby incorporated by reference herein. A flow directed device can be advanced through the introducer into the flow of blood and permitted to be carried thereby downstream past the dissection D into the descending aorta. More generally sternotomy can be used as a retrograde approach to aortic valve or proximal ascending aorta or as antegrade approach of Type III dissections initiating very close to the subclavian artery, or thoracic aortic aneurysms starting at the distal part of the arch (between left carotid & left subclavian).

Before or while the flow directed device is being inserted, a snare can be positioned in the descending aorta downstream of the dissection D at a position where the snare can capture the flow directed device. Thereafter, the snare can be pulled retrograde past the dissection and out of the incision I to be accessible through the SA device. Or the flow directed device can be drawn by the snare downstream into a catheter body from which the snare is deployed. The snare and/or flow directed device provide a structure to pull or advance a guidewire without risk of extending the dissection. Once the guidewire is placed, a treatment device as in FIG. 5 can be delivered from the peripheral arterial site, through the incision or both from the peripheral arterial site and through the incision.

In a variation of the methods discussed above in connection with FIG. 11, surgical access is provided by way of a thoracotomy procedure. In this variation, the surgical access SA may be at a location downstream of the left subclavian artery, e.g., at the aortic isthmus. Once such surgical access is provided, dissections can be treated with the graft device 200 using the rail techniques disclosed herein ether upstream or downstream of the surgical access SA. For example, a De Bakey Type II dissection can be treated in this manner by advancing a graft device through the thoratcotomy-based surgical access SA counter to blood flow along the rail. The dissection may be located as shown in FIG. 1A. Thoracotomy access can be used for antegrade access for some type III dissections or descending aortic thoracic aneurysms.

Figure 12:
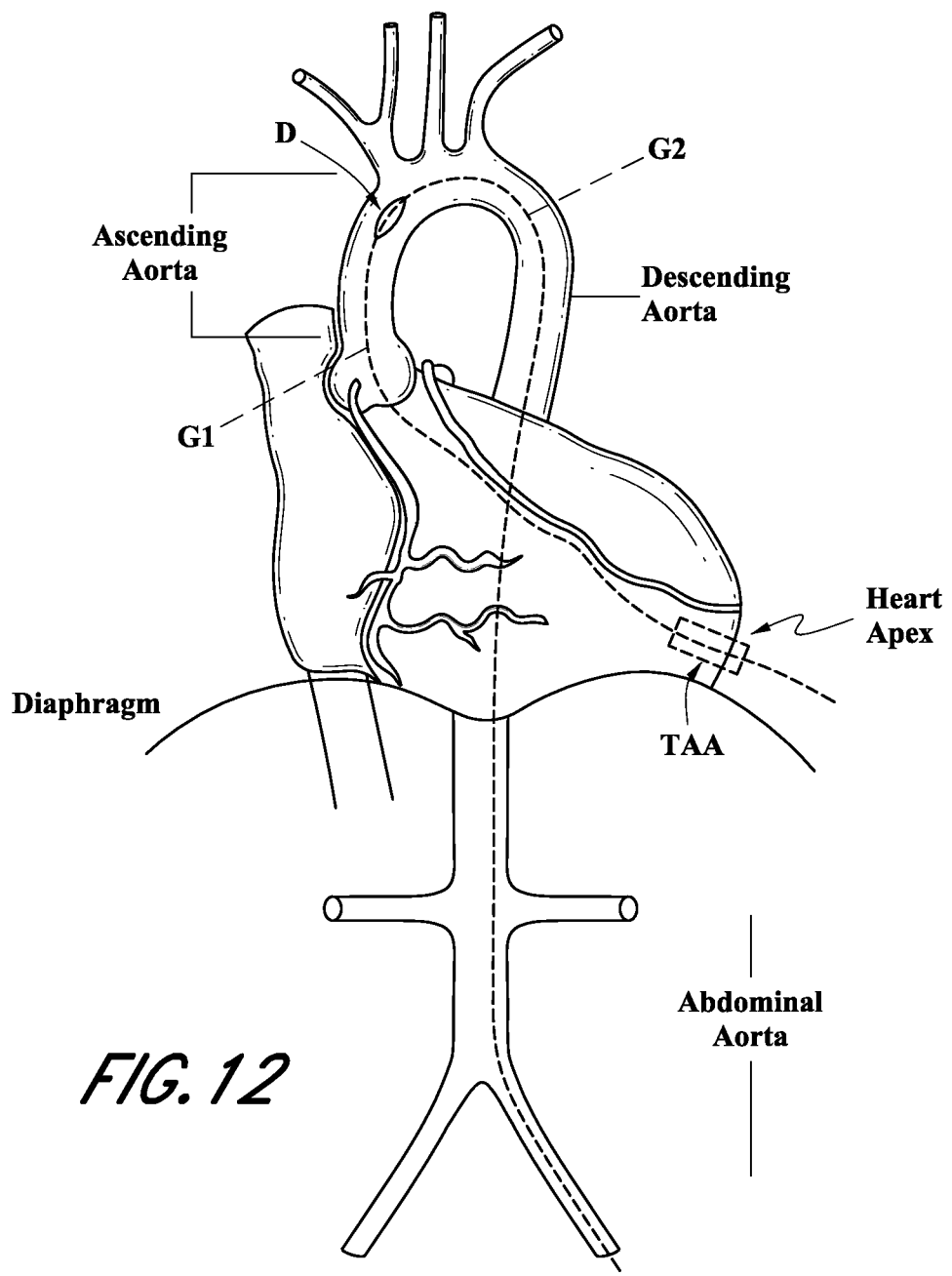
FIG. 12 illustrates a trans-apical access approach.

FIG. 12 shows another technique to safely establishing an approach to a dissection D for treatment thereof. In this approach, trans-apical access (TAA) device is provided through the left ventricle apex of the heart. The TAA device can include a port or sleeve to enable other catheters to be delivered into the heart. An example of such a device is described in WO2011/017440, which is incorporated by reference in its entirety.

A flow directed device can be advanced through the TAA device into the left ventricle after the TAA device is positioned. Such a device will be carried by the blood through the left ventricular outflow tract and across the aortic valve as discussed above. In other embodiments, a catheter is advanced through the left ventricular outflow tract and across the aortic valve. The flow directed device is expelled from the heart and flows along the path G1 through a portion of the aorta upstream of the dissection D. In the illustrated embodiment, the dissection D is in the distal ascending aorta. The flow directed device is carried into the arch and into the proximal descending aorta. Similar to techniques discussed above, a device can be advanced from a peripheral arterial site along the path G2. The device can include a catheter having a snare disposed therein. A continuous track can be established by capturing the flow directed device with the snare, such that the paths G1 and G2 are joined. This will provide a continuous path from the TAA to the peripheral arterial site. In variants of this method, the snare and flow directed device are replaced by a wire along which a treatment device can be safely advanced.

FIG. 12 illustrates that the peripheral arterial site will be downstream of the iliac arterials, e.g., through the femoral arteries. Other peripheral arterials could be used in this technique, e.g., including the subclavian artery, the common carotid artery, or the brachial artery in the arm. In case of miniaturization of devices, a radial approach could be used, as discussed above.

Although FIGS. 11 and 12 illustrate treatment of a dissection, aneurysm and other maladies that would benefit from a stent, a graft, a stent-graft or other support device can be placed using these techniques.

Although the present invention has been disclosed with reference to certain specific embodiments of devices and methods, the inventor contemplates that the invention more broadly relates to methods disclosed above, such as those useful for positioning aneurysm treatment devices, including stent-grafts, in blood vessels. For instance, one could place a treatment device, including stent-graft, in the ascending aorta and/or in the descending aorta, the abdominal aorta, and/or a segment of a blood vessel between a peripheral arterial site and the aorta. One could place a treatment device, including stent-graft, in the ascending aorta and/or in a venous blood vessel section between a peripheral venous site and the superior or inferior vena cava. Accordingly, the present invention is not intended to be limited to the specific structures and steps disclosed herein, but rather by the full scope of the attached claims.

What is claimed is:

1. A method for positioning a device in a blood vessel of a patient adjacent to the heart, the method comprising
   advancing a venous catheter endoluminally from a venous site to the heart;
   advancing an elongate member from the venous catheter through a valve in the heart to a blood vessel adjacent to the heart;
   advancing an arterial catheter endoluminally from an arterial site toward the heart;
   drawing the elongate member into the arterial catheter;
   advancing the arterial catheter over the elongate member such that tip portions of the venous and arterial catheters are brought into adjacency; and
   deploying a device within the blood vessel from a platform extending from the venous catheter to the arterial site, the blood vessel being adjacent to the heart.

2. The method of claim 1, wherein the elongate member comprises a flow directed device.

3. The method of claim 1, further comprising positioning the tip portions adjacent to but spaced away from each other.

4. The method of claim 1, further comprising coupling the tip portions with each other.

5. The method of claim 1, wherein the elongate body comprises a flow directed catheter.

6. The method of claim 5, wherein drawing the elongate body into the arterial catheter comprises extending a snare from the tip portion of the arterial catheter and capturing the flow directed catheter with the snare.

7. The method of claim 1, wherein the elongate member comprises a snare.

8. The method of claim 1, wherein the arterial site is located at a peripheral superficial blood vessel.

9. The method of claim 1, wherein the arterial site is disposed in a brachial artery.

10. The method of claim 1, wherein the arterial site is disposed in an axillary artery.

11. The method of claim 1, wherein the arterial site is disposed in a subclavian artery.

12. The method of claim 1, wherein the arterial site is a common carotid artery.

13. The method of claim 1, wherein deploying a device comprises:
    advancing a graft device disposed on, over or within the platform to a position within a aorta of the patient;
    positioning the graft device at a treatment site within the aorta; and
    expanding the graft device into apposition with the aorta.

14. The method of claim 13, wherein the treatment site includes a dissection in an ascending segment of the aorta.

15. The method of claim 13, wherein the treatment site includes a dissection in a descending segment of the aorta.

16. The method of claim 13, wherein the treatment site includes a dissection in an arch of the aorta.

17. The method of claim 1, wherein device comprises a stent-graft.

18. A method for positioning a device in a blood vessel of a patient adjacent to the heart, the method comprising:
    advancing a venous catheter endoluminally from a venous site to the heart: advancing a snare from the venous catheter through a valve in the heart to a blood vessel adjacent to the heart:
    advancing a shaped wire endoluminally from an arterial site toward the heart;
    drawing the shaped wire into the venous catheter using the snare to provide a rail from the arterial site to the venous site;
    advancing an arterial catheter over the shaped wire such that tip portions of the venous and arterial catheters are brought into adjacency; and
    deploying a device within the blood vessel from a platform extending from the venous catheter to the arterial site, the blood vessel being adjacent to the heart.

19. The method of claim 18, wherein deploying a device comprises:
    advancing a graft device disposed on, over or within the platform to a position within an ascending aorta of the patient;
    positioning the graft device at a treatment site within the aorta; and
    expanding the graft device into apposition with the aorta.

20. The method of claim 19, wherein the treatment site includes a dissection in an ascending segment of the aorta.

21. The method of claim 19, wherein the treatment site includes a dissection in a descending segment of the aorta.

22. The method of claim 19, wherein the treatment site includes a dissection in an arch of the aorta.

23. The method of claim 18, wherein device comprises a stent-graft.

\* \* \* \* \*